United States Patent
Somberg

(10) Patent No.: US 11,344,518 B2
(45) Date of Patent: *May 31, 2022

(54) METHOD OF CONVERTING ATRIAL FIBRILLATION TO NORMAL SINUS RHYTHM AND LOADING ORAL SOTALOL IN A SHORTENED TIME FRAME

(71) Applicant: AltaThera Pharmaceuticals LLC, Chicago, IL (US)

(72) Inventor: John Somberg, Chicago, IL (US)

(73) Assignee: AltaThera Pharmaceuticals LLC, Chicago, IL (US)

( * ) Notice: Subject to any disclaimer, the term of this patent is extended or adjusted under 35 U.S.C. 154(b) by 74 days.

This patent is subject to a terminal disclaimer.

(21) Appl. No.: 16/946,941

(22) Filed: Jul. 13, 2020

(65) Prior Publication Data

US 2020/0338027 A1    Oct. 29, 2020

Related U.S. Application Data

(63) Continuation-in-part of application No. 16/863,567, filed on Apr. 30, 2020, and a continuation-in-part of application No. 16/849,099, filed on Apr. 15, 2020, now abandoned, said application No. 16/863,567 is a continuation-in-part of application No. 16/693,310, filed on Nov. 24, 2019, and a continuation-in-part of application No. 16/693,312, filed on Nov. 24, 2019, which is a continuation of application No. 16/103,815, filed on Aug. 14, 2018, now Pat. No. 10,512,620, said application No. 16/693,310 is a continuation-in-part of application No. 16/103,815, filed on Aug. 14, 2018, now Pat. No. 10,512,620.

(60) Provisional application No. 63/009,511, filed on Apr. 14, 2020, provisional application No. 62/987,832, filed on Mar. 10, 2020.

(51) Int. Cl.
*A61P 9/06*    (2006.01)
*A61K 31/18*   (2006.01)
*A61K 9/00*    (2006.01)

(52) U.S. Cl.
CPC ............ *A61K 31/18* (2013.01); *A61K 9/0019* (2013.01); *A61P 9/06* (2018.01)

(58) Field of Classification Search
None
See application file for complete search history.

(56) References Cited

U.S. PATENT DOCUMENTS

| | | |
|---|---|---|
| 6,043,273 A | 3/2000 | Duhaylongsod |
| 6,060,454 A | 5/2000 | Duhaylongsod |
| 6,101,412 A | 8/2000 | Duhaylongsod |
| 6,136,327 A | 10/2000 | Gupta et al. |
| 6,281,246 B2 | 8/2001 | Sankaranarayanan |
| 6,369,114 B1 | 4/2002 | Weil et al. |
| 6,482,811 B1 | 11/2002 | Bacaner et al. |
| 6,491,039 B1 | 12/2002 | Dobak, III |
| 6,500,459 B1 | 12/2002 | Chhabra et al. |
| 6,627,223 B2 | 9/2003 | Percel et al. |
| 6,632,217 B2 | 10/2003 | Harper et al. |
| 6,720,001 B2 | 4/2004 | Chen et al. |
| 6,800,668 B1 | 10/2004 | Odidi et al. |
| 6,899,700 B2 | 5/2005 | Gehling et al. |
| 7,004,171 B2 | 2/2006 | Benita et al. |
| 7,005,425 B2 | 2/2006 | Belardinelli et al. |
| 7,022,343 B2 | 2/2006 | Philbrook et al. |
| 7,048,945 B2 | 5/2006 | Percel et al. |
| 7,090,830 B2 | 8/2006 | Hale et al. |
| 7,179,597 B2 | 2/2007 | Woosley |
| 7,341,737 B2 | 3/2008 | Gehling et al. |
| 7,371,254 B2 | 5/2008 | Dobak, III |
| 7,417,038 B1 | 8/2008 | Anker et al. |
| 7,526,335 B2 | 4/2009 | Ferek-Petric |
| 7,538,092 B2 | 5/2009 | Orlando et al. |
| 7,815,936 B2 | 10/2010 | Hasenzahl et al. |
| 7,829,573 B2 | 11/2010 | Curwen et al. |
| 7,951,183 B2 | 5/2011 | Dobak, III |
| 8,263,125 B2 | 9/2012 | Vaya et al. |
| 8,268,352 B2 | 9/2012 | Vaya et al. |
| 8,313,757 B2 | 11/2012 | van Lengerich |
| 8,377,994 B2 | 2/2013 | Gray et al. |
| 8,399,018 B2 | 3/2013 | Lichter et al. |
| 8,440,168 B2 | 5/2013 | Yang et al. |
| 8,465,769 B2 | 6/2013 | Petereit et al. |
| 8,466,277 B2 | 6/2013 | Orlando et al. |
| 8,696,696 B2 | 4/2014 | Solem |
| 8,709,076 B1 | 4/2014 | Matheny et al. |
| 8,753,674 B2 | 6/2014 | Helson |

(Continued)

OTHER PUBLICATIONS

Barbey, J.T., et al., "Pharmacokinetic, pharmacodynamic, and safety evaluation of an accelerated dose titration regimen of sotalol in healthy middle-aged subjects," Clin. Pharmacol. Ther. 66(1):91-99, Mosby, Inc., United States (1999).

(Continued)

*Primary Examiner* — Robert T. Crow
*Assistant Examiner* — John P Nguyen
(74) *Attorney, Agent, or Firm* — New River Valley IP Law, P.C.; Michele L. Mayberry

(57) ABSTRACT

The present invention provides a novel method of converting AF and monitoring normal sinus rhythm using an initial IV dose of sotalol followed by oral sotalol maintenance therapy. This method provides a method of acute assessment of QTc prolongation to determine the safety of chronic oral sotalol therapy and reduces the hospitalization stay required for conversion and sotalol initiation.

11 Claims, No Drawings

(56) References Cited

U.S. PATENT DOCUMENTS

| | | |
|---|---|---|
| 8,828,432 B2 | 9/2014 | van Lengerich |
| 8,865,213 B2 | 10/2014 | Sheth et al. |
| 8,871,452 B2 | 10/2014 | Lee |
| 8,906,847 B2 | 12/2014 | Cleemann et al. |
| 8,987,262 B2 | 3/2015 | Leaute-Labreze et al. |
| 9,011,526 B2 | 4/2015 | Matheny |
| 9,044,319 B2 | 6/2015 | Matheny |
| 9,060,969 B2 | 6/2015 | Matheny |
| 9,078,929 B2 | 7/2015 | Kuebelbeck et al. |
| 9,161,952 B2 | 10/2015 | Matheny et al. |
| 9,239,333 B2 | 1/2016 | Snider |
| 9,308,084 B2 | 4/2016 | Matheny |
| 9,474,719 B2 | 10/2016 | Mullen et al. |
| 9,554,989 B2 | 1/2017 | Kaplan et al. |
| 9,585,851 B2 | 3/2017 | Fun et al. |
| 9,616,026 B2 | 4/2017 | Singh |
| 9,682,041 B2 | 6/2017 | Helson |
| 9,724,297 B2 | 8/2017 | Thomas et al. |
| 10,512,620 B1 | 12/2019 | Somberg et al. |
| 10,799,138 B2 | 10/2020 | Ivaturi et al. |
| 2007/0009564 A1 | 1/2007 | McClain et al. |
| 2007/0009654 A1 | 1/2007 | McClain et al. |
| 2012/0003318 A1* | 1/2012 | Schuler .......... A61K 31/55 128/200.14 |
| 2014/0235631 A1 | 8/2014 | Bunt et al. |
| 2014/0276404 A1 | 9/2014 | Orlowski |
| 2015/0081010 A1 | 3/2015 | Matheny |
| 2015/0210712 A1 | 7/2015 | Blumberg et al. |
| 2016/0082159 A1 | 3/2016 | Orlowski |
| 2016/0128944 A1 | 5/2016 | Chawrai et al. |
| 2016/0228379 A1 | 8/2016 | Kumar et al. |
| 2016/0271070 A1 | 9/2016 | Singh et al. |
| 2016/0271157 A1 | 9/2016 | Ahmed et al. |
| 2016/0303133 A1 | 10/2016 | Dudley et al. |
| 2016/0317388 A1 | 11/2016 | Bhargava et al. |
| 2017/0049705 A1 | 2/2017 | Mateescu et al. |
| 2017/0100387 A1 | 4/2017 | Arora et al. |
| 2017/0119627 A1 | 5/2017 | Bhargava et al. |
| 2017/0157076 A1 | 6/2017 | Yacoby-Zeevi et al. |
| 2017/0231885 A1 | 8/2017 | Cremers et al. |
| 2017/0296493 A1 | 10/2017 | Thomas et al. |
| 2017/0348303 A1 | 12/2017 | Bosse et al. |
| 2018/0071390 A1 | 3/2018 | Patel et al. |
| 2019/0307343 A1 | 10/2019 | Ivaturi et al. |
| 2019/0380605 A1 | 12/2019 | Ivaturi et al. |
| 2020/0085771 A1 | 3/2020 | Somberg et al. |
| 2020/0093759 A1 | 3/2020 | Somberg et al. |
| 2020/0226481 A1 | 7/2020 | Sim et al. |
| 2020/0253903 A1 | 8/2020 | Somberg |
| 2021/0076959 A1 | 3/2021 | Ivaturi et al. |
| 2021/0283049 A1 | 9/2021 | Somberg |

OTHER PUBLICATIONS

Ho, D.S.W., et al., "Rapid intravenous infusion of d-l sotalol: time to onset of effects on ventricular refractoriness, and safety," European Heart Journal 16:81-86, European Society of Cardiology, United Kingdom (1995).

Läer, S., et al., "Development of a safe and effective pediatric dosing regimen for sotalol based on population pharmacokinetics and pharmacodynamics in children with supraventricular tachycardia," J. American College of Cardiology 46(7):1322-1330, Elsevier, Inc., United States (2005).

Lynch, J.J., et al., "Prevention of ventricular fibrillation by dextrorotatory sotalol in a conscious canine model of sudden coronary death," American Heart Journal 109(5):949-958, Elsevier, Inc., United States (1985).

Neumar, R.W., et al., "Part 8: Adult Advanced Cardiovascular Life Support," Circulation 122(3):S729-S767 (2010).

Snider, M., et al., "Initial experience with antiarrhythmic medication monitoring by clinical pharmacists in an outpatient setting: a retrospective review," Clinical Therapeutics 31(6):1209-1218, Excerpta Medica, Inc., United States (2009).

Somberg, J.C., et al., "Developing a Safe Intravenous Sotalol Dosing Regimen," American Journal of Therapeutics 17:365-372, Lippincott Williams & Wilkins, United States (2010).

Somberg, J.C., et al., "Gender Differences in Cardiac Repolarization Following Intravenous Sotalol Administration," J. Cardiovasc. Pharmacol. Ther. 17(1):86-92, Sage, United States (2012).

Yarlagadda, B., et al., "Safety and Efficacy of Inpatient Initiation of Dofetilide Versus Sotalol for Atrial Fibrillation," J. Atrial Fibrillation 10(4):1805, Cardiofront, United States (2017).

Saul, J.P., et al., "Pharmacokinetics and pharmacodynamics of sotalol in a pediatric population with supraventricular and ventricular tachyarrhythmia," Clinical Pharma & Therapeutics 69(3): 145-157, United States, 2001.

El-Assaad, I., et al., "Lone Pediatric Atrial Fibrillation in the United States: Analysis of Over 1500 Cases," Pediatr. Cardiol. 38:1004-1009, Springer Publishing, United States (2017).

Galloway, C.D., et al., "Development and Validation of a Deep-Learning Model to Screen for Hyperkalemia From the Electrocardiogram," JAMA Cardiol.: E1-E9, American Medical Association, United States (Apr. 3, 2019).

Hannun, A.Y., et al., "Cardiologist-level arrhythmia detection and classification in ambulatory electrocardiograms using a deep neural network," Nature Medicine 25:65-69, Nature Publishing, United States (Jan. 2019).

Marill, K.A., et al., "Meta-analysis of the Risk of Torsades de Pointes in Patients Treated with Intravenous Racemic Sotalol," Academic Emergency Medicine 8(2):117-124, Wiley, United States (2001).

Peters, F.P.J., et al., "Treatment of recent onset atrial fibrillation with intravenous solalol and/or flecainide," Netherlands Journal of Medicine 53:93-96, Elsevier Science B.V., Netherlands (1998).

Radford, D.J., et al., "Atrial Fibrillation in Children," Pediatrics 59(2):250-256, American Academy of Pediatrics, United States (1977).

Thomas, S.P., et al., "Rapid loading of sotalol or amiodarone for management of recent onset symptomatic atrial fibrillation: A randomized, digoxin-controlled trial," Am. Heart J. 147:e3 (6 pages), Elsevier Inc., Netherlands (2004).

Li, X. et al., "Efficacy of Intravenous Sotalol for Treatment of Incessant Tachyarrhythmias in Children," Am. J. Cardiol. 119:1366-70, United States (2017).

Batul, S. A., et al., "Intravenous Sotalol—Reintroducing a Forgotten Agent to the Electrophysiology Therapeutic Arsenal," J. Atr. Fibr. 9(5):85-89, United States, 2017.

Gomes, J.A., et al., "Oral d,l Sotalol Reduces the Incidence of Postoperative Atrial Fibrilation in Coronary Artery Bypass Surgery Patients: A Randomized, Double-Blind, Placebo-Controlled Study," J. Am. Coll. Cardio. 34(2):334-9, US 1999.

Dahmane, E. et al., Clinical Pharmacology-Driven Translational Research to Optimize Bedside Therapeutics of Sotalol Therapy, Clin. Transl. Sci 2019, 12, 648-656.

Patel, A. et al., Is Sotalol more effective than standard beta-blockers for prophylaxis of atrial fibrillation during cardia surgery? Interactive Cardiovascular and Thoracic Surgery 2005, 4, 147-150.

Campbell, T. J. et al., Intraveneous sotalol for the treatment of atrial fibrillation and flutter after cardiopulmonary bypass Comparison with disopyramide and digoxiin in a randomised trial. Br. Heart J. 1985, 54, 86-90.

Kerin, Nicholas Z., Intravenous Sotalol: An Under Used Treatment Strategy. Cardiology 2018, 140, 143-145.

Sanjuan, R. et al., Preoperative Use of Sotalol Versus Atenolol for Atrial Fibrillation After Cardiac Surgery. Ann. Thorac. Surg. 2004, 77, 838-43.

Li, X. et al., Pediatric Dosing of Intraveneous Sotalol Based on Body Surface Area in Patients with Arrhythmia. Pediatr. Cardiol. 2017, 38, 140-55.

Tse, H.-F., et al., Atrial pacing for suppression of early reinitiation of atrial fibrillation after successful internal cardioversion. European Heart Journal (2000) 21, 1167-1176.

Peters, N. S., Post-cardioversion atrial fibrillation: the synthesis of modern concepts? European Heart Journal (2000) 21, 1119-1121.

Co-Pending U.S. Appl. No. 17/566,840, Petition Under 37 CFR 1.181 and Preliminary Amendment, dated Feb. 22, 2022, 9 pages.

(56) References Cited

OTHER PUBLICATIONS

Co-Pending U.S. Appl. No. 17/585,190, Preliminary Amendment dated Mar. 4, 2022, 4 pages.
Dumas, M. et al., "Variations of sotalol kinetics in renal insufficiency", International Journal of Clinical Pharmacology, Therapy, and Toxicology, Oct. 1, 1989, 27(10), Abstract only.
FDA Highlights of Prescribing Information sotalol hydrochloride injection (2009), https://www.accessdata.fda.gov/drugsatfda_docs/label/2009/022306s000lbl.pdf.
FDA Highlights of Prescribing Information Sotylize (sotalol hydrochloride (2014), https://www.accessdata.fda.gov/drugsatfda_docs/label/2014/205108s000lbl.pdf.
Hoffman et al. "Renal Insufficiency and Medication in Nursing Homes" Medicine Deutsches Arzteblatt International 2016; 113: 92-98.
Somberg, J.C., "QT prolongation and serum sotalol concentration are highly correlated following intravenous and oral sotalol," Cardiology (2010) 116(3):219-25.
Sundquist, H.K. et al., "Serum levels and half-life of sotalol in chronic renal failure", Annals of Clinical Research, Dec. 1, 1975, 7(6), Abstract Only.
U.S. Appl. No. 16/376,706 (U.S. Pat. No. 10,799,138), file history Dec. 2020, 151 pages.
Vaides, S.O., "early experience with intravenous sotalol in children with and without congenital heart disease," Heart Rhythm 15(12): 1862-1869, Elsevier Inc., (Jul. 9, 2018).
U.S. Appl. No. 63/009,511, filed Apr. 14, 2020, John Charin Somberg.
(Devlin, Jodi) Co-pending U.S. Appl. No. 17/566,840, filed Dec. 31, 2021, Specification, Claims, and Figures.
(Ivaturi, Vijay et al.) U.S. Appl. No. 16/376,706, filed Apr. 5, 2019, Specification, Claims, Figures.
(Ivaturi, Vijay et al.) U.S. Appl. No. 16/549,620, filed Aug. 23, 2019, Specification, Claims, Figures and File History as of Dec. 2020, 77 pages (abandoned).
(Ivaturi, Vijay et al.) U.S. Appl. No. 17/003,297, filed Aug. 26, 2020, Specification, Claims, Figures.
(Somberg, John C. et al.) Co-Pending U.S. Appl. No. 16/103,815, filed Aug. 14, 2018, Specification, Claims, Figures.
(Somberg, John C. et al.) Co-Pending U.S. Appl. No. 16/693,310, filed Nov. 24, 2019, Specification, Claims, Figures.
(Somberg, John C. et al.) Co-Pending U.S. Appl. No. 16/693,312, filed Nov. 24, 2019, Specification, Claims, Figures.
(Somberg, John C. et al.) Co-Pending U.S. Appl. No. 16/726,361, filed Dec. 24, 2019, Specification, Claims, Figures.
(Somberg, John) Co-Pending U.S. Appl. No. 16/849,099, filed Apr. 15, 2020, Specification and Claims.
(Somberg, John) Co-Pending U.S. Appl. No. 16/863,567, filed Apr. 30, 2020, Specification and Claims.
(Somberg, John) Co-Pending U.S. Appl. No. 17/306,490, filed May 3, 2021, Specification and Claims.
(Somberg, John) Co-Pending U.S. Appl. No. 17/585,190, filed Jan. 26, 2022, Specification and Claims.
U.S. Appl. No. 17/003,297, Preliminary Amendment filed Dec. 8, 2020, 9 pages.
Blair, Andrew D., et al., Sotalol kinetics in renal insufficiency, Clin. Pharmacol. Ther., 457-463 (Apr. 1981) (7 pages).
Co-Pending U.S. Appl. No. 16/103,815, Final Office Action dated Aug. 13, 2019, 13 pages.
Co-Pending U.S. Appl. No. 16/103,815, Non-Final Office Action dated Feb. 6, 2019, 9 pages.
Co-Pending U.S. Appl. No. 16/103,815, Notice of Allowance dated Oct. 30, 2019, 12 pages.
Co-Pending U.S. Appl. No. 16/103,815, Response to Aug. 13, 2019 Final Office Action, filed Oct. 17, 2019, 10 pages.
Co-Pending U.S. Appl. No. 16/103,815, Response to Dec. 13, 2018 Restriction Requirement, filed Dec. 31, 2018, 3 pages.
Co-Pending U.S. Appl. No. 16/103,815, Response to Feb. 6, 2019 Non-Final Office Action, filed May 6, 2019, 17 pages.
Co-Pending U.S. Appl. No. 16/103,815, Restriction Requirement dated Dec. 13, 2018, 6 pages.
Co-Pending U.S. Appl. No. 16/376,706, Final Office Action dated Mar. 27, 2020, 12 pages.
Co-Pending U.S. Appl. No. 16/376,706, Non-final Office Action dated Nov. 12, 2019, 12 pages.
Co-Pending U.S. Appl. No. 16/376,706, Notice of Allowance and Examiner Initiated Interview Summary dated Jun. 10, 2020, 8 pages.
Co-Pending U.S. Appl. No. 16/376,706, Response to Mar. 27, 2020 Final Office Action dated May 27, 2020, 11 pages.
Co-Pending U.S. Appl. No. 16/376,706, Response to Nov. 12, 2019 Non-Final Office Action filed Feb. 12, 2020, 10 pages.
Co-Pending U.S. Appl. No. 16/693,310, Final Office Action dated Sep. 3, 2021, 20 pages.
Co-Pending U.S. Appl. No. 16/693,310, Non-Final Office Action dated Feb. 7, 2020, 12 pages.
Co-Pending U.S. Appl. No. 16/693,310, Petition Decision dated Mar. 29, 2021, 2 pages.
Co-Pending U.S. Appl. No. 16/693,310, Response to Feb. 7, 2020 Non-Final Office Action, filed May 5, 2020, 20 pages.
Co-Pending U.S. Appl. No. 16/693,310, Response to Sep. 3, 2021 Final Office Action, dated Feb. 3, 2022, 7 pages.
Co-Pending U.S. Appl. No. 16/693,312, Final Office Action dated Mar. 29, 2021, 14 pages.
Co-Pending U.S. Appl. No. 16/693,312, Non-Final Office Action dated Jan. 7, 2022, 15 pages.
Co-Pending U.S. Appl. No. 16/693,312, Non-Final Office Action dated Oct. 20, 2020, 17 pages.
Co-Pending U.S. Appl. No. 16/693,312, Response to Mar. 29, 2021 Final Office Action, filed Sep. 29, 2021, 13 pages.
Co-Pending U.S. Appl. No. 16/693,312, Response to Oct. 20, 2020 Non-Final Office Action, filed Feb. 22, 2021, 11 pages.
Co-Pending U.S. Appl. No. 16/849,099, Final Office Action dated Feb. 3, 2021, 24 pages.
Co-Pending U.S. Appl. No. 16/849,099, Non-Final Office Action dated Jul. 9, 2020, 19 pages.
Co-Pending U.S. Appl. No. 16/849,099, Notice of Abandonment, dated Aug. 20, 2021, 2 pages.
Co-Pending U.S. Appl. No. 16/849,099, Response to Jul. 9, 2020 Non-Final Office Action, dated Dec. 9, 2020, 10 pages.
Co-Pending U.S. Appl. No. 16/863,567, Advisory Action dated Dec. 30, 2021, 11 pages.
Co-Pending U.S. Appl. No. 16/863,567, Final Office Action dated Dec. 28, 2020, 17 pages.
Co-Pending U.S. Appl. No. 16/863,567, Final Office Action dated Oct. 26, 2021, 11 pages.
Co-Pending U.S. Appl. No. 16/863,567, Non-Final Office Action and Examiner Initiated Interview Summary dated Jun. 9, 2021, 14 pages.
Co-Pending U.S. Appl. No. 16/863,567, Non-Final Office Action dated Jun. 4, 2020, 18 pages.
Co-Pending U.S. Appl. No. 16/863,567, Response to Jun. 4, 2020 Non-Final Office Action dated Dec. 4, 2020, 10 pages.
Co-Pending U.S. Appl. No. 16/863,567, Response to Jun. 9, 2021 Non-Final Office Action dated Oct. 12, 2021, 8 pages.
Co-Pending U.S. Appl. No. 16/863,567, Response to May 13, 2020 Restriction Requirement, filed May 26, 2020, 44 pages.
Co-Pending U.S. Appl. No. 16/863,567, Response to Oct. 26, 2021 Final Office Action, dated Dec. 10, 2021, 8 pages.
Co-Pending U.S. Appl. No. 16/863,567, Restriction Requirement dated May 13, 2020, 5 pages.
U.S. Appl. No. 17/003,297, Non-Final Office Action dated Mar. 14, 2022, 14 pages.
Co-Pending U.S. Appl. No. 17/566,840, Non-Final Office Action dated Mar. 23, 2022, 11 pages.
Learn the Heart, "Antiarrhythmic Drug Review," https://www.healio.com/cardiology/learn-the-heart/cardiology-review/topic-reviews/antiarrhythmic-drugs (Year: 2022).

* cited by examiner

METHOD OF CONVERTING ATRIAL FIBRILLATION TO NORMAL SINUS RHYTHM AND LOADING ORAL SOTALOL IN A SHORTENED TIME FRAME

CROSS-REFERENCE TO RELATED APPLICATION

This application claims the benefit of:
and is a continuation-in-part of U.S. application Ser. No. 16/863,567 filed 30 Apr. 2020:
  which claims priority to U.S. Provisional Application No. 63/009,511 filed 14 Apr. 2020;
  which is a continuation-in-part of U.S. application Ser. No. 16/693,310, filed 24 Nov. 2019, which is a continuation-in-part of U.S. application Ser. No. 16/103,815, filed 14 Aug. 2018, now U.S. Pat. No. 10,512,620; and, which is a continuation-in-part of U.S. application Ser. No. 16/693,312 filed 24 Nov. 2019, which is a continuation of U.S. application Ser. No. 16/103,815, filed 14 Aug. 2018, now U.S. Pat. No. 10,512,620; and,
and is a continuation-in-part of U.S. application Ser. No. 16/849,099 filed 15 Apr. 2020, which claims priority to U.S. Provisional Application No. 62/987,832 filed 10 Mar. 2020;
  of which their entirety is incorporated herein by reference.

FIELD OF THE INVENTION

The present invention provides a novel method of converting atrial fibrillation to normal sinus rhythm and loading oral sotalol in a shortened time frame in patients with paroxysmal or persistent atrial fibrillation.

BACKGROUND OF THE INVENTION

Patients with paroxysmal or persistent atrial fibrillation (AF) have a significant medical burden. They have a very significant increased risk of embolization. In addition, AF is associated with bothersome symptoms of palpitation, weakness and "fluttering" in the neck and throat areas. AF is associated with a reduced cardiac output and can lead to the development of heart failure.

Li et al (Am. J. Cardiol. 2017, 119, 1366-70) describes studies of treating incessant tachyarrhythmias in children with IV sotalol. Some successes were obtained for patients with atrioventricular reentrant tachycardia (converted within 2 hours, but on IV sotalol 3-26 hours before oral sotalol "transition"), persistent atrial tachycardia, atrial flutter, atrial fibrillation, or ventricular tachycardia (if converted within 24 hours of IV sotalol, kept on IV sotalol for another 24 hours before oral sotalol "transition") and atrioventricular reentrant tachycardia (on IV sotalol for 1-24 hours before oral sotalol "transition"). Li does not describe what oral sotalol "transition" means in terms of dosages, post IV timing, or dosage frequency.

Batul (JAFIB 2017, 9(5), 85-89) describes how IV sotalol could be a useful form of sotalol due to the ability to both more easily vary sotalol dosage and to achieve therapeutic dosages more quickly. While Batul does note that IV sotalol "could be potentially useful in hospital initiation of sotalol and to facilitate transition to oral sotalol[,]" no further mention is made as to what this would look like other than that further studies are needed. In addition, Batul is silent regarding the possibility (or even idea) of converting AF to NSR and initiating oral sotalol all within a shortened time frame.

While intravenous (IV) sotalol has been demonstrated to convert atrial fibrillation (AF) to normal sinus rhythm (NSR) (see, for example, Thomis et al. Am. Heart J. 2004; 147 e3, where a rapid infusion of sotalol cause AF conversion to sinus rhythm in 44% of patients), the FDA has not approved IV sotalol to terminate AF. This is due to sotalol's prolongation of the QT interval and thus the risk of Torsade de Points-a life threatening ventricular arrhythmia caused by drugs that prolong the QT interval, such as sotalol. Therefore, the FDA has mandated with a "black box" warning that sotalol must be loaded in hospital over a three-day period. This can mean that a patient who is converted will still need to be hospitalized for days in order to be initiated on oral sotalol. However, if the QTc prolongation caused by sotalol is not excessive, sotalol is a safe way to terminate AF (Tse et al. European Heart J. 2000; 21:1167-1169.

Thus, it would be beneficial to discover a method of converting AF and loading sotalol in a shortened timeframe that allows for the initial determination of QTc effect and thus safety of the sotalol prolonged oral therapy to prevent AF recurrence (which without therapy occurs often).

SUMMARY OF THE INVENTION

Accordingly, in an aspect, the present invention provides a novel method of converting atrial fibrillation (AF) and initiating oral sotalol in a shortened time frame, comprising: intravenously (IV) administering sotalol hydrochloride to a patient with paroxysmal or persistent atrial fibrillation to convert the AF to normal sinus rhythm and then orally administering sotalol hydrochloride in order to initiate the patient for chronic oral sotalol.

In another aspect, the present invention provides a novel method of both converting AF and initiating oral sotalol within 24 hours of IV initiation.

These and other aspects, which will become apparent during the following detailed description, have been achieved by the inventors' discovery that sotalol can simultaneously treat paroxysmal or persistent atrial fibrillation and be initiated in a short period of time.

DETAILED DESCRIPTION OF THE INVENTION

All references cited herein are hereby incorporated in their entirety herein by reference.
AF is atrial fibrillation.
NSR is normal sinus rhythm.
IV is intravenous.
PO is "per os" and refers to an oral dosing regimen.
BID is "bis in die" and means twice a day dosing.
Patient (or subject) refers to a human patient.
BP is blood pressure.
HR is heart rate.
QT is the interval measured from the start of the Q wave or the QRS complex, to the end of the T wave, where the Q wave corresponds to the beginning of ventricular depolarization and the T wave end corresponds to the end of ventricular repolarization.
QTc is the calculated interval that represents the QT interval corrected for heart rate and can be derived by simple mathematical correlation of the QT interval and the heart rate.
ΔQTc is the difference between a QTc measurement taken prior to the start of IV sotalol and a QTc measured after the start of IV sotalol (e.g., during loading or maintenance).

Sotalol and sotalol hydrochloride (used interchangeably herein) refer to d,l-sotalol hydrochloride which has been approved by the FDA for intravenous administration over 5 hours and oral administration (e.g., 80 mg, 120 mg, and 160 mg tablets) to be administered twice daily.

Hospital refers to a medical facility staffed and equipped for cardiac surgeries and can provide continuous ECG monitoring and cardiac resuscitation to patients, if needed.

Shortening the length of a hospital stay refers to the length of time a patient is admitted for treatment of paroxysmal or persistent atrial fibrillation combined with initiation of oral sotalol. Currently the FDA recommends a 72 hour stay just for oral sotalol initiation.

Therapeutically effective amount refers to an amount of sotalol that will convert AF to NSR.

Accordingly, in an aspect, the present invention provides a novel method of converting atrial fibrillation (AF) and initiating oral sotalol, comprising:

a. intravenously (IV) administering sotalol hydrochloride over 1 h to a patient with paroxysmal or persistent AF to convert the AF to normal sinus rhythm (NSR); and,
   b. orally administering sotalol hydrochloride BID after AF conversion.

Some of the benefits of administering IV sotalol include (a) converting AF to NSR, (b) achieving C max in 1 h, and (c) determining the extent of QT prolongation and thus long term sotalol tolerability (safety). If the IV Sotalol converts AF to NSR using the 1 h IV dosing and it is then followed by oral dosing (e.g., 5 hours post IV infusion) and again in 12 h (after the $1^{st}$ oral dosage—this is BID dosing), one can convert AF, assess QT effects (safety evaluation) and obtain oral sotalol loading all in a 24 hr. period. This enables a patient to undergo pharmacologic conversion and loading of sotalol in a 24 hr. period. This is compared to current treatment which requires conversion of AF followed by oral sotalol initiation, which would be expected to require at least 72 hours of hospitalization.

NSR is determined by ECG recording that occurs during and following IV sotalol administration.

Currently AF is converted in the majority of cases by electrical conversions, the application of DC shock across the chest directed at the heart. This requires anesthesia and still may be very uncomfortable for the patient. Pharmacologic conversion of AF may take up to 12 hours and is not recommended for certain drugs such as sotalol because of excessive QTc prolongation and the possibility of arrhythmias. Using the present IV infusion, the drug can be stopped if QTc is excessively prolonged, avoiding arrhythmias developing. In this way, the IV sotalol administration can establish safety and in about half the cases avoid cardiac shock. Patients who don't convert may receive electrical cardioversion and have the sotalol "on board" to prevent AF re-occurrence once in sinus rhythm.

In the present invention, the physician of a patient who is suffering from paroxysmal or persistent AF selects a dose of oral sotalol that would be targeted (e.g., 80 mg, 120 mg, or 160 mg) and then the IV load is determined based on the targeted oral dosage. As shown in Table 1, the IV Load and Maintenance are based on the targeted oral sotalol dosage of 80, 120, or 160 mg (the currently FDA approved oral dosages).

TABLE 1

| IV Sotalol Load and Maintenance Protocol | | | |
|---|---|---|---|
| Target dose* (mg) | 80 | 120 | 160 |
| IV Load (mg over 1 h) | 65 | 95 | 125 |
| Time to first oral dose (h) | 5 | 5 | 5 |

*Selected by patient's physician/surgeon.

The present IV loading strategy is based on pharmacometric modeling and simulations that match the acute concentration of sotalol achieved by IV administration to the peak sotalol blood concentration following an oral dose of the medications. Thus, in one hour a peak concentration, which is proportional to peak QTc effect, can be observed that matches the highest QTc to be seen with chronic oral dosing. If the highest QTc with oral dosing is within acceptable increments, the risk of developing life-threatening arrhythmias due to sotalol is very significantly diminished.

The IV load, as shown in Table 1, is typically administered over 1 hour. Additional examples of the time over which the IV load is administered, include 50-70 minutes. Further examples include 50, 51, 52, 53, 54, 55, 56, 57, 58, 59, 60, 61, 62, 63, 64, 65, 66, 67, 68, 69, and 70 minutes.

Additional examples of the IV load for the target dose of 80 mg include 55-85 mg. Further examples include 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, and 85 mg.

Additional examples of the IV load for the target dose of 120 mg include 75-115 mg. Further examples include 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, and 115 mg.

Additional examples of the IV load for the target dose of 160 mg include 100-150 mg. Further examples include 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, and 150 mg.

In another aspect, the BID oral administration is started 2, 3, 4, 5, 6, 7, to 8 hours after completion of IV sotalol. Further examples include (a) 3-7, (b) 4-6 hours, and (c) 5 hours.

In another aspect, the BID oral administration is started 2, 3, 4, 5, 6, 7, to 8 hours after conversion of AF to NSR. Further examples include (a) 3-7, (b) 4-6 hours, and (c) 5 hours.

Once on oral therapy (BID), it is maintained at the patient's physician's discretion, but it is typically chronic therapy (long-lasting). For example, the oral therapy can be continued for days (1, 2, 3, 4, 5, 6, or 7), weeks (1, 2, 3, or 4), months (1, 2, 3, 4, 5, 6, 7, 8, 9, 10, 11, or 12), or even years.

In another aspect, the present invention provides a novel method shortening the length of a patient's hospital stay, comprising:

a. intravenously (IV) administering sotalol hydrochloride over 1 h to a patient with paroxysmal or persistent AF to convert the AF to normal sinus rhythm (NSR); and,
   b. orally administering sotalol hydrochloride BID after AF conversion.

A typical hospital stay for a patient requiring treatment for paroxysmal or persistent AF (conversion) and oral sotalol initiation is 3-5 days. The presently method allows for both conversion and sotalol initiation to be completed in 1 hospital day.

In another aspect the IV loading dose is 65 mg and the oral dose is 80 mg.

In another aspect the IV loading dose is 95 mg and oral dose is 120 mg.

In another aspect the IV loading dose is 125 mg and the oral dose is 160 mg.

In another aspect, the patient's QTc is monitored via electrocardiography.

In another aspect, the patient's QTc is measured at baseline (prior to sotalol administration) and then measured periodically thereafter (e.g., every 15 or 30 minutes during loading). The QTc can be measured at other intervals if more (shorter time period) or less data (longer time periods) data is desired. The QTc is also typically monitored for 15-30 minutes after completion of the IV administration.

In another aspect, the patient's QTc interval is monitored every 15 (or 30) minutes after intravenous sotalol hydrochloride initiation (and throughout the time the patient remains on IV sotalol). If the patient's QTc is observed to be greater than 500 msec or if the ΔQTc is greater than or equal to 20% of the subject's QTc prior to sotalol administration, the IV sotalol is discontinued.

In another aspect, the HR and BP the patient is monitored every 15 minutes (or 30 minutes) during IV administration. If a BP below 90 mmHg and HR<50 bpm are observed, then the IV is discontinued. The HR and BP are also typically monitored for 15-30 minutes after completion of the IV administration.

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

Other features of the invention will become apparent in the course of the following descriptions of exemplary embodiments that are given for illustration of the invention and are not intended to be limiting thereof.

EXAMPLES

Example 1

A male patient, age 60, diagnosed with 3-vessel coronary artery disease has a history of intermittent AF. The decision is made to convert the AF the patient is currently in and place the patient on long-term oral sotalol therapy. The patient is admitted to the hospital, placed on continuous electrocardiography monitoring and then loaded with 65 mg of sotalol via a 1-hour IV infusion. The patient's QT is measured prior to the IV start and monitored every 15 minutes during the IV load along with HR and BP. The patient's QTc is calculated from the QT measurement. If the patient's QTc is observed to be greater than 500 msec or if the ΔQTc is greater than 20% of the subject's QTc prior to sotalol administration, the IV sotalol infusion is slowed, reduced in concentration, or discontinued at the physicians discretion. Following the one-hour infusion of IV Sotalol, the patient converts from AF to normal sinus rhythm at a HR of 80 bpm.

Five hours after the start of the infusion the patient receives his first oral dose of sotalol 80 mg orally. Twelve hours following the first oral dose (17 hours after the start of the infusion) the patient receives a second oral dose of 80 mg orally and then every 12 hours thereafter. The patient remains in normal sinus rhythm and is discharged in 24 hours from the hospital (a one-day hospitalization).

After the first or second oral doses, the maintenance dose is discontinued if the patient's QTc is observed to be greater than 500 msec or if the ΔQTc is greater than the subject's QTc prior to sotalol administration.

Example 2

A 73-year-old patient has been in AF for several months but feels excessively weak and fatigued. She asks her physician if she can be returned to her prior more vigorous health. It is decided to convert the patient and she is placed on oral anticoagulant. Six weeks later she is admitted to the hospital and receives an IV infusion of 95 mg of IV Sotalol with HR, BP and QTc monitored at baseline and every 15 minutes for 90 minutes. All goes well, in the course of the infusion the patient converts to NSR. Five hours following the infusion the patient receives 120 mg orally of sotalol, 3 hours later QTc, HR and BP are within normal range and 17 hours after the start of the IV Sotalol the patient receives a second oral dose of 120 mg sotalol. The patient remains in normal sinus rhythm and is discharged in 24 hours from the hospital (a one-day hospitalization).

Numerous modifications and variations of the present invention are possible considering the above teachings. It is therefore to be understood that within the scope of the appended claims, the invention may be practiced otherwise that as specifically described herein.

What is claimed is:

1. A method of converting atrial fibrillation (AF) and initiating oral sotalol, comprising:
   a. administering an intravenous (IV) dose of sotalol hydrochloride over a period of 1 hour to a hospitalized patient with paroxysmal or persistent atrial fibrillation (AF) to convert the AF to normal sinus rhythm (NSR); and,
   b. administering oral dosing of sotalol hydrochloride at a 12-hour interval, wherein the oral dosing is initiated after the AF conversion;
   c. wherein the sotalol hydrochloride is administered in an amount in the range of:
      100-150 mg as the IV dose based on an oral target dose of 160 mg; and
      135-165 mg as an oral dose.

2. The method of claim 1, wherein the oral dosing is initiated after completion of the IV dose.

3. The method of claim 1, wherein the oral dosing is initiated 4-6 hours after completion of the IV dose.

4. The method of claim 1, wherein the patient is discharged from the hospital 24 hours after IV initiation.

5. The method of claim 1, wherein the IV dose is 105 mg sotalol hydrochloride.

6. The method of claim 1, wherein the oral dose is 160 mg.

7. The method of claim 5, wherein the oral dose is 160 mg.

8. The method of claim 1, further comprising administering additional oral dose(s) of sotalol hydrochloride.

9. The method of claim 7, further comprising administering additional oral dose(s) of sotalol hydrochloride.

10. The method of claim 8, wherein one or more of the additional oral doses are administered at a 12-hour interval from initiation of the oral dosing.

11. The method of claim 9, wherein one or more of the additional oral doses are administered at a 12-hour interval from initiation of the oral dosing.

\* \* \* \* \*